(12) United States Patent
Nicita

(10) Patent No.: US 7,985,174 B2
(45) Date of Patent: Jul. 26, 2011

(54) DEVICE FOR THE SURGICAL TREATMENT OF FEMALE PROLAPSE

(75) Inventor: Giulio Nicita, Florence (IT)

(73) Assignee: FIN MED S.a.s. di Grondelli & C., Parma (IT)

( * ) Notice: Subject to any disclaimer, the term of this patent is extended or adjusted under 35 U.S.C. 154(b) by 1577 days.

(21) Appl. No.: 10/523,144

(22) PCT Filed: Aug. 1, 2003

(86) PCT No.: PCT/EP03/08546
§ 371 (c)(1),
(2), (4) Date: Nov. 3, 2005

(87) PCT Pub. No.: WO2004/012626
PCT Pub. Date: Feb. 12, 2004

(65) Prior Publication Data
US 2006/0134159 A1 Jun. 22, 2006

(30) Foreign Application Priority Data
Aug. 1, 2002 (IT) ................. FI2002A0145

(51) Int. Cl.
*A61F 13/00* (2006.01)

(52) U.S. Cl. ........................................... 600/37; 600/30
(58) Field of Classification Search .............. 600/29–32, 600/37
See application file for complete search history.

(56) References Cited

U.S. PATENT DOCUMENTS

| 6,042,534 | A | 3/2000 | Gellman et al. | |
| 6,355,065 | B1 * | 3/2002 | Gabbay | 623/11.11 |
| 6,436,030 | B2 * | 8/2002 | Rehil | 600/37 |
| 2002/0058980 | A1 * | 5/2002 | Sass | 607/116 |
| 2002/0099258 | A1 | 7/2002 | Anderson et al. | 600/29 |
| 2002/0107430 | A1 * | 8/2002 | Neisz et al. | 600/37 |
| 2003/0212460 | A1 * | 11/2003 | Darois et al. | 623/23.64 |

FOREIGN PATENT DOCUMENTS

| EP | 0 774 240 | 5/1997 |
| WO | WO 00/64370 | 11/2000 |

* cited by examiner

*Primary Examiner* — Charles A Marmor, II
*Assistant Examiner* — Carrie Dorna
(74) *Attorney, Agent, or Firm* — Abelman, Frayne & Schwab

(57) ABSTRACT

A device is described having a reticular or laminar structure to be surgically implanted in uro-gynaecological treatments, useful in particular for the surgical treatment of total or partial prolapse of the female pelvic organs or of prolapse of the vaginal vault.

16 Claims, 6 Drawing Sheets

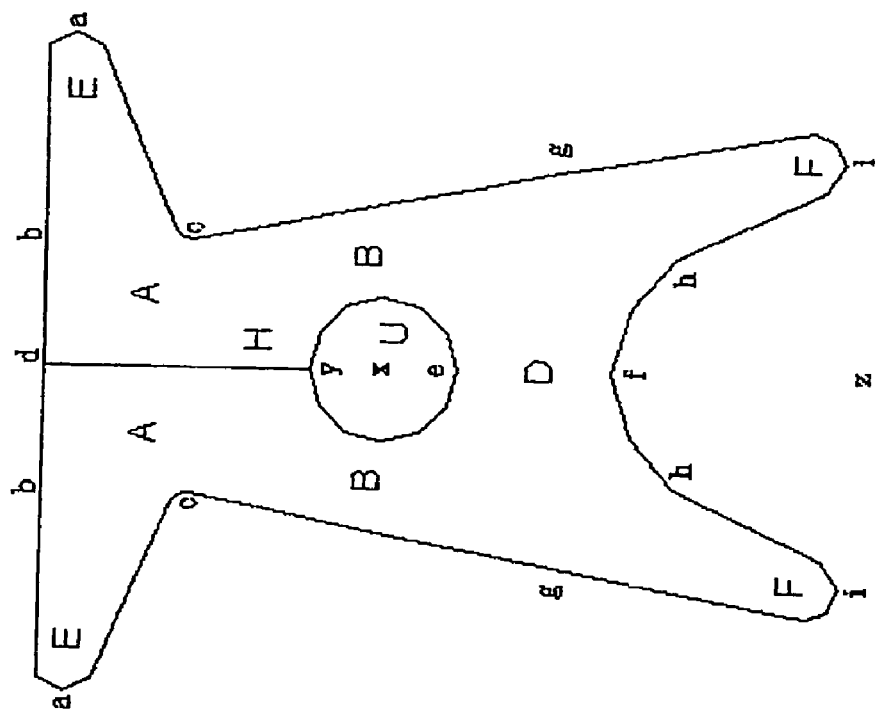
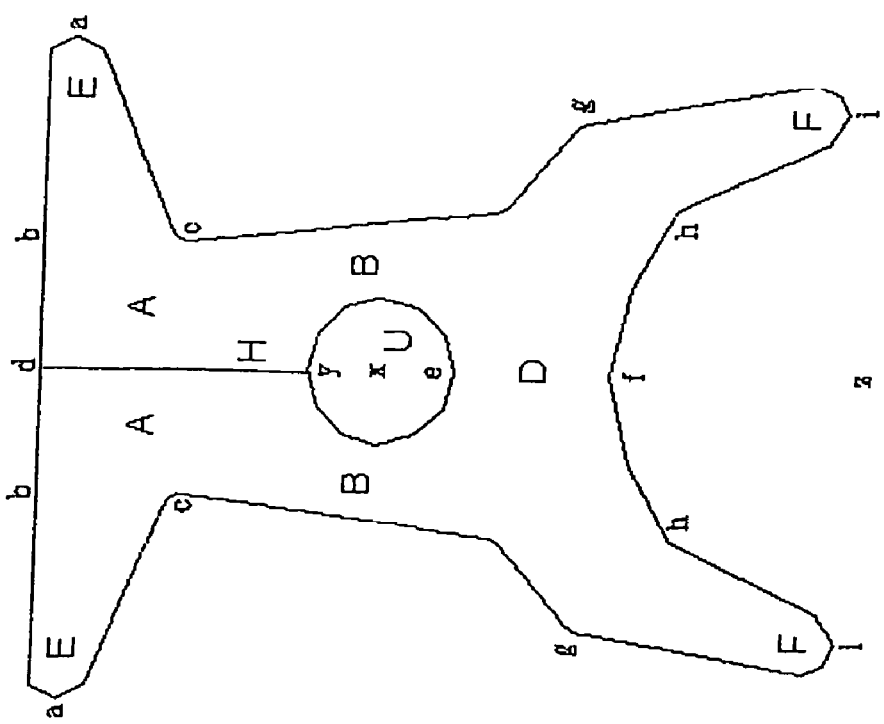

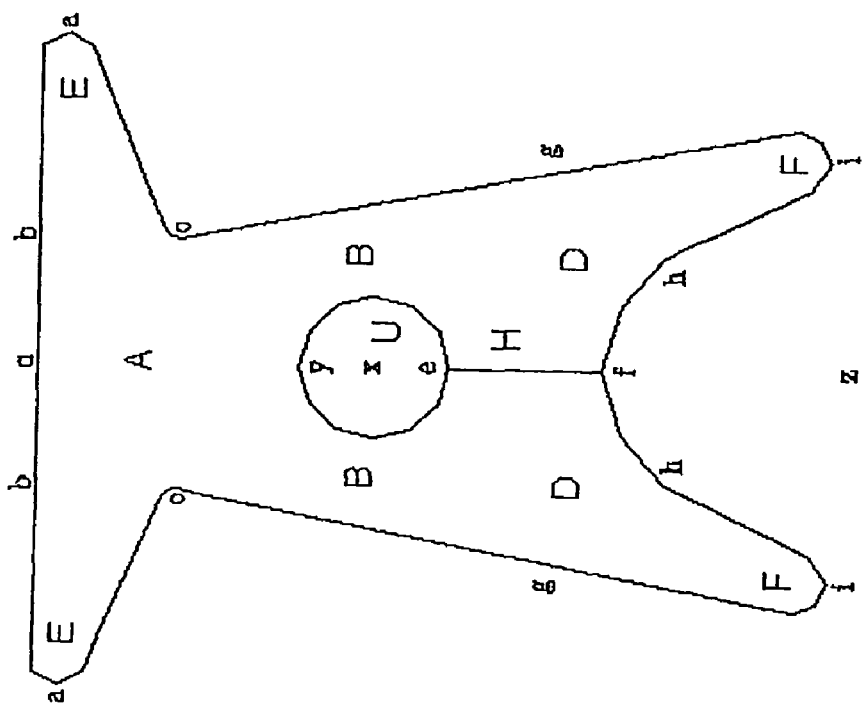
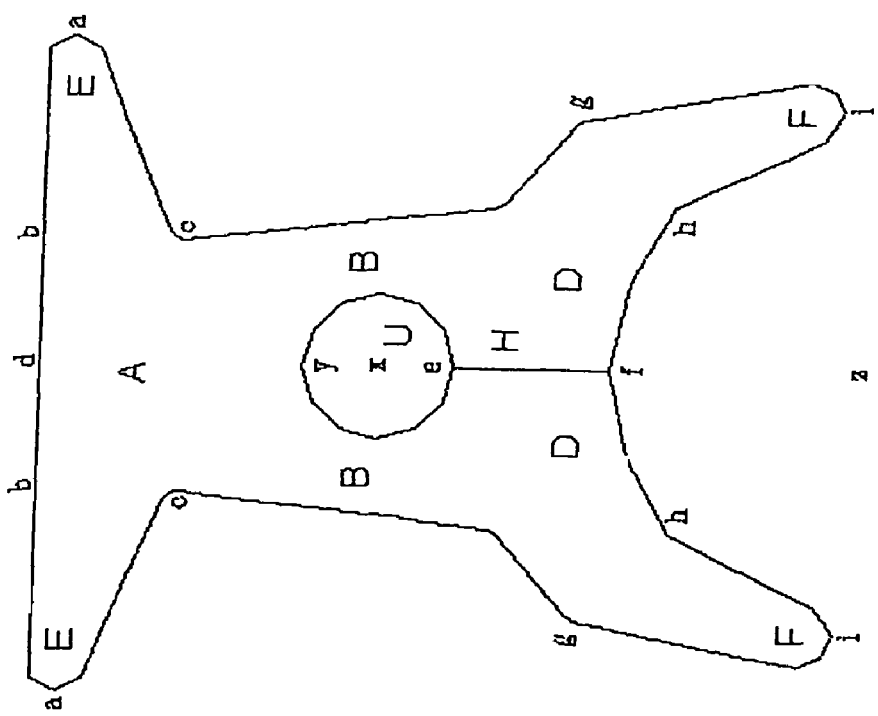

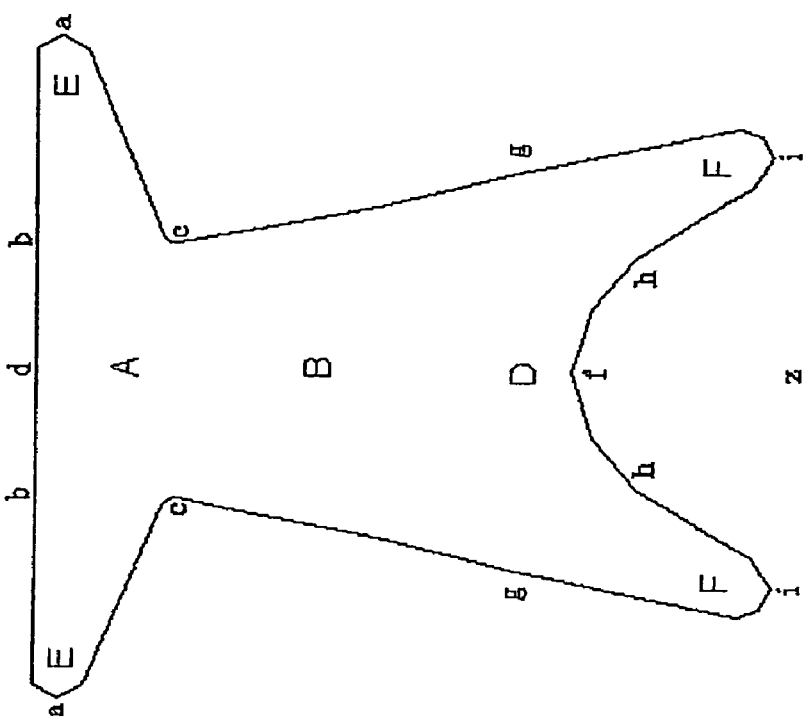
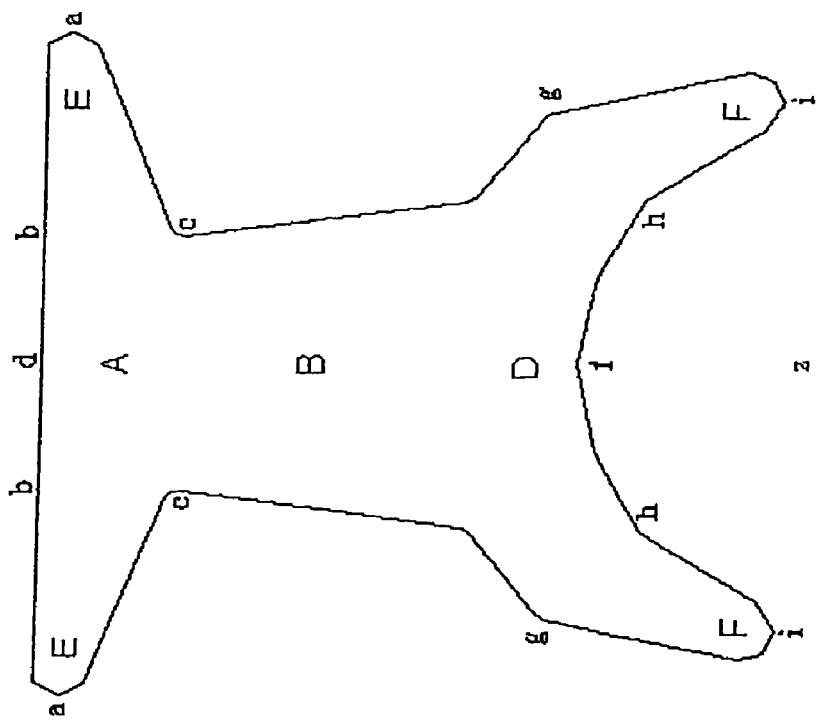

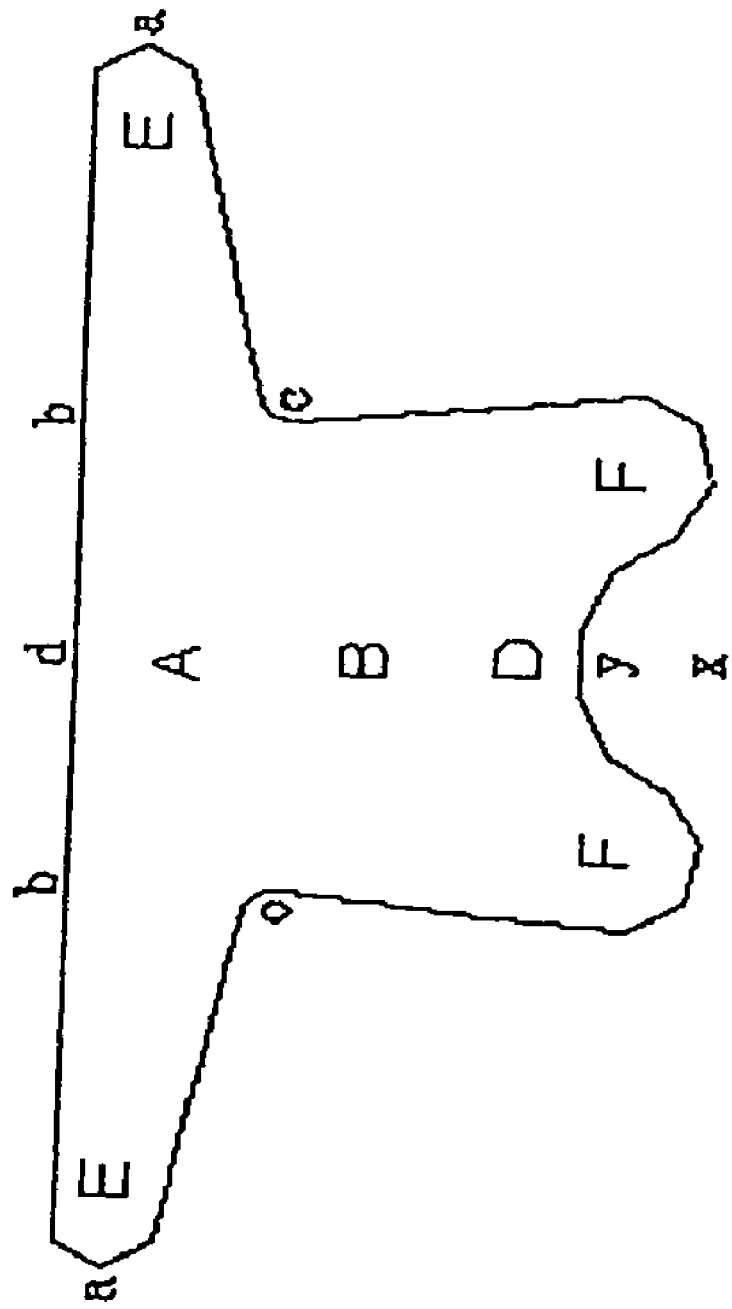

DEVICE FOR THE SURGICAL TREATMENT OF FEMALE PROLAPSE

FIELD OF THE INVENTION

The present invention concerns a device for supporting the female pelvic organs, to be surgically implanted in uro-gynaecological treatments.

STATE OF THE ART

The term "female prolapse" means the sinking or displacement through the vagina of a female pelvic organ, bladder, uterus or rectum, which may occur for only one of these organs or for more than one organ simultaneously.

In the case where the prolapse concerns the bladder, there is protrusion of the front vaginal wall, known as "cystocele", in the case where the prolapse concerns the uterus, there is sinking of the upper vaginal wall, known as "hysterocele"; whereas the terms "enterocele" and "rectocele" are used when the vaginal wall affected by sinking is the rear wall and also comprises prolapse of the rectum.

When all the pelvic organs—bladder, uterus and rectum—are involved, the term used is "total prolapse" and in this case the whole vagina is affected by the sinking of the internal organs, to the extent that there is often a real evagination of the vagina.

In patients who have already had a hysterectomy, and are therefore without uterus, there may be "prolapse of the vaginal vault", in which sinking principally involves the bladder and the intestine.

Prolapse is a fairly frequent problem in women and may occur following a difficult vaginal birth or problems of the connective tissues.

Moreover, prolapse often appears in association with other disturbances, such as urinary or faecal incontinence. As may be easily imagined, female prolapse can therefore have important affects on the quality of life and may cause severe limitations in daily living.

While there may be various approaches to treatment for incontinence, even pharmacological, depending on the diagnosis, the treatment of female prolapse is exclusively surgical.

Up till now, in fact, the problem of female prolapse has been solved by surgically removing the uterus. The operation provides a remedy to the contingent situation for a short time but, as it leaves an empty space where the removed organ had been, it increases the probability of sinking of other internal organs.

A further disadvantage is that surgical operations of this type require total anaesthesia of the patient, who will also require relatively long periods of hospitalisation and convalescence.

Devices have recently appeared on the market which, when surgically implanted, allow support of the urethra and of the neck of the bladder, and are therefore useful for correcting only urinary incontinence due to stress.

SUMMARY OF THE INVENTION

The Applicant has now found a reticular or laminar device which, when surgically implanted, provides support for the female pelvic organs in the case of prolapse of the vaginal vault or partial or total prolapse through the vagina.

This device therefore makes it possible to overcome the inconvenient aspects described above concerning the prior surgical technique: the device according to the invention may in fact be vaginally, mixed vaginally/abdominally or vaginally/laparoscopically implanted, or implanted by means of mini-invasive surgery, requiring in the majority of cases only local anaesthesia, the hospitalisation and convalescence times are considerably reduced and no organ is removed.

It is therefore subject of the invention a flat implantable device made of material with a reticular or laminar structure for supporting the female pelvic organs, characterised in that it has a central body with a trapezoid shape having four arms, in which may be distinguished:

a front portion corresponding to the smaller base of the trapezium, from the ends of which branch off in opposite directions two arms coaxial with each other and parallel to said smaller base;

a central portion corresponding to the central part of the trapezium;

a rear portion corresponding to the larger base of the trapezium, from the ends of which branch off two arms diverging from each other and parallel to the sides of the trapezium.

BRIEF DESCRIPTION OF THE DRAWINGS

FIG. 1: front view of the present device having a hole in the central portion and the front portion divided into two halves by longitudinal cleft. FIGS. 1a and 1b differ for dimensions, respectively adapted for bigger and smaller patient body sizes.

FIG. 2: front view of the present device having a hole in the central portion and the rear portion divided into two halves by longitudinal cleft. FIGS. 2a and 2b differ for dimensions, respectively adapted for bigger and smaller patient body sizes.

FIG. 3: front view of the present device without the hole in the central portion and the longitudinal cleft. FIGS. 3a and 3b differ for dimensions, respectively adapted for bigger and smaller patient body sizes.

FIG. 4: front view of the present device without the hole in the central portion and having the rear arms shorter than in the devices of FIGS. 1-3.

DETAILED DESCRIPTION OF THE INVENTION

As a non limiting example of the invention:

FIG. 1a represents a front view of the device according to the invention constituted by a central body, in which may be distinguished a front portion A intended to hold the prolapsed bladder (cystocele), a rear portion D on which is placed the prolapsed intestine (enterocele), and a central portion B with the hole U which holds the uterus. The portions A, B and D into which the central body is subdivided are suitably shaped and have dimensions such as to be able to hold and support the prolapsed organs.

From the front portion A branch off the two arms E, while from the rear portion D branch off the two arms F; both pairs of arms are suitably shaped and positioned with respect to the longitudinal axis of the device in such a way that they can be anchored, during surgery, to fixed and well Identified structures on the patient's pelvis.

Central portion B has a width, the maximum dimension of which is designated W. Front arms A and rear arms F respectively have terminal ends spaced apart from each other a distance greeter than dimension W.

In the device represented in FIG. 1a the front portion A of the central body is divided into two halves by a longitudinal cleft H, the purpose of which is to divaricate during surgery the device already anchored through the rear arms F, so as to pass the two halves D from opposite sides with respect to the uterus and to be able to place the neck of the uterus more easily in the hole U.

FIG. 1b represents another front view of the device according to the invention, in which the dimensions, in particular those of the rear arms F and of the rear portion D, have been reduced to adapt the device to a smaller patient body size. The present device may also be realised as in FIG. 2a, with the longitudinal cleft H which cuts the rear portion D of the central body in two halves; this device adapts to a type of surgical implant in which the front arms E are anchored first, then the rear part D is divaricated thanks to the cleft H so as to facilitate the entry of the neck of the uterus in the hole U, and lastly the rear arms F are anchored.

FIG. 2b represents the same type of device with the cleft H in the rear portion D shown in FIG. 2a, in which the dimensions of the device have been reduced to adapt it to patients of a smaller size.

A further embodiment of the present device contemplates that the cleft H is present both in the front part and in the rear, thus cutting the device in two halves which are then rejoined at the time of surgery.

Figure 6:
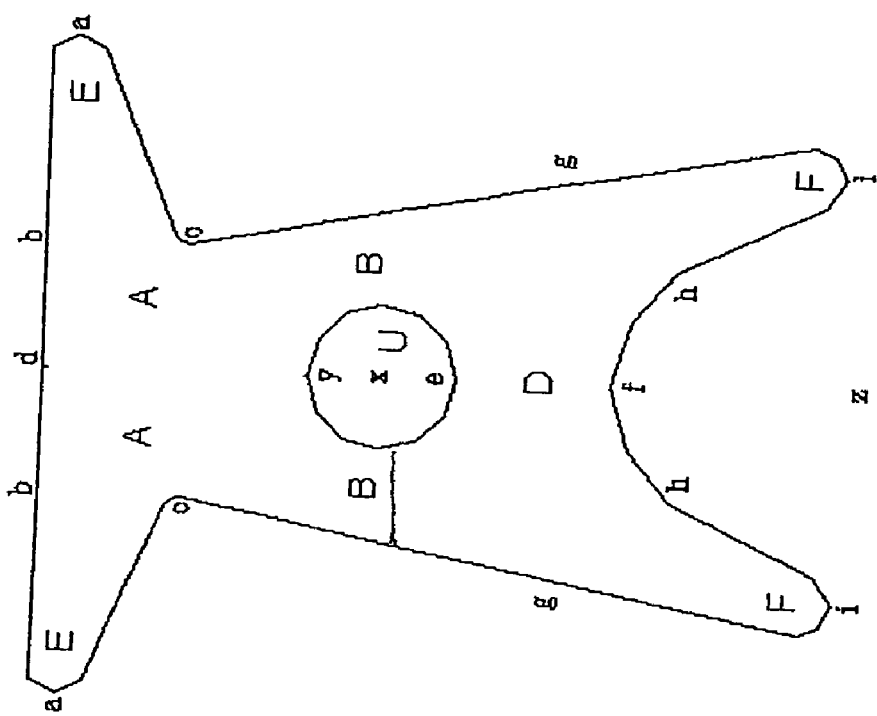
FIG. 6: front view of another embodiment of the present invention showing a cleft to the left from the hole in the central portion.
Figure 5:
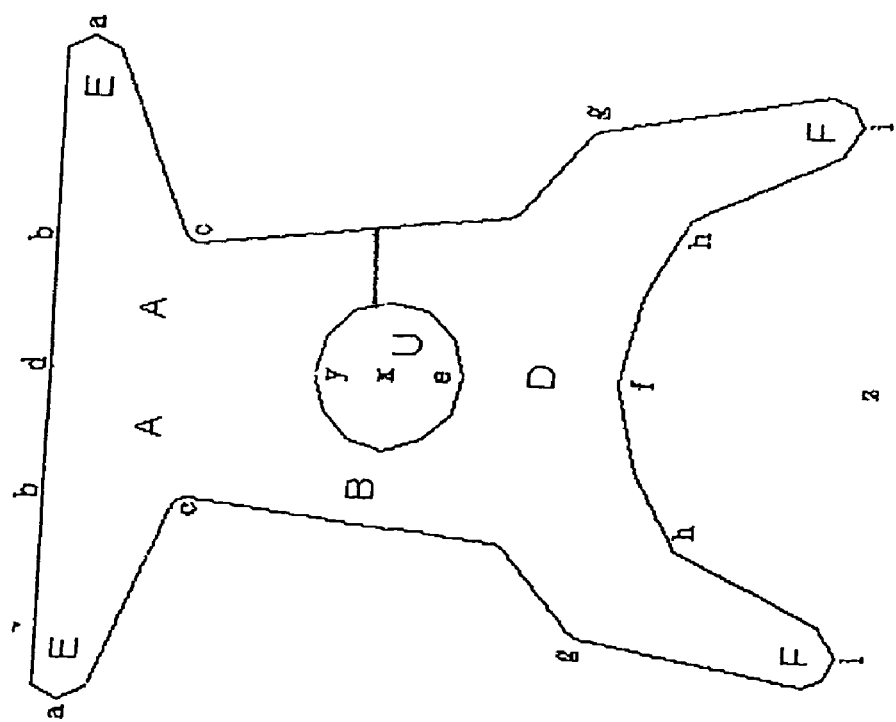
FIG. 5: front view of another embodiment of the present invention showing a cleft to the right from the hole in the central portion.
Figure 7:
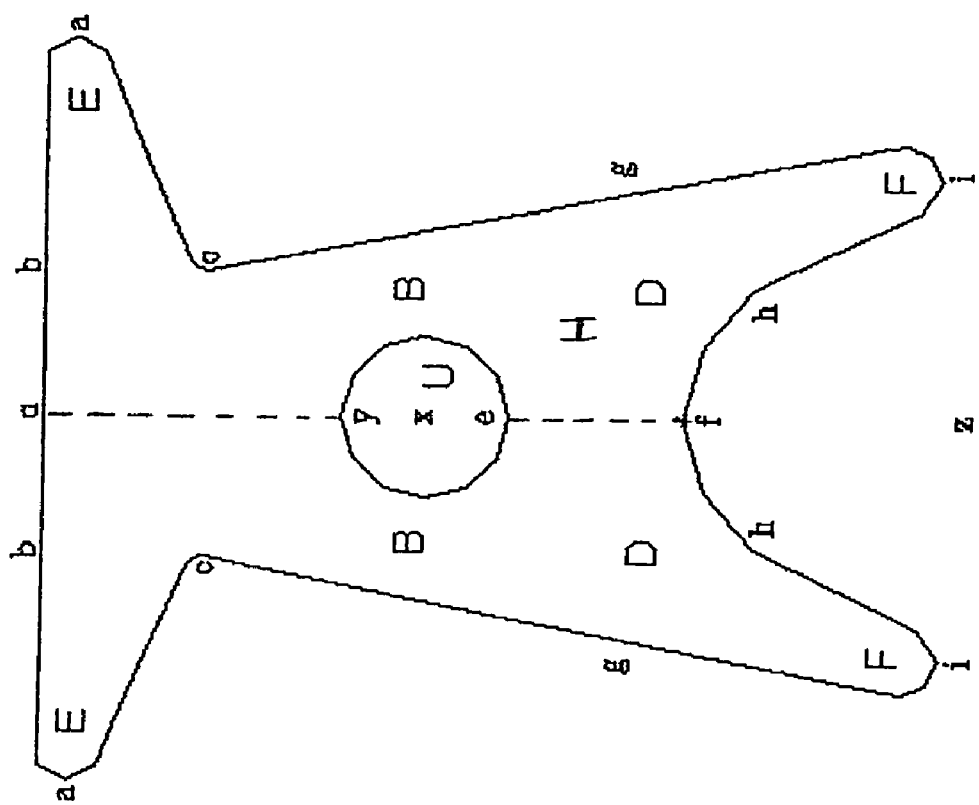
FIG. 7: front view of still another embodiment showing central longitudinal lines extending to both the front and rear, representing clefts by which the device is formed into a set of halves that are rejoinable during surgery.

According to a further embodiment of the invention, the present invention has a central hole and a transverse cleft H which, starting from the central hole, cuts the central portion to the right of the hole, or the one to the left, in two halves, as seen in FIGS. 5 and 6 respectively.

FIG. 3a represents the device according to the invention without the central hole U to be used, depending on the dimensions of the rear arms F described in greater detail below, in cases of prolapse of the vaginal vault in patients without uterus, or in cases of partial prolapse.

FIG. 3b represents the same type of device for patients of a smaller size.

With reference to FIGS. 1-3, the dimensions of the device according to the invention are for example the following:
- length a-a of the front arms E: between 8.0 and 15 cm; when the device is implanted by means of "tension free" operations, the length a-a is typically between 11 and 15 cm, and is preferably 13 cm; while for all the other types of surgical implant it is typically between 8.0 and 12.0 cm and is preferably 10 cm;
- length b-b of the front portion A: between 2.5 and 6.0 cm, and preferably 3.8 cm;
- length c-c of the front portion A: between 3.0 and 6.0 cm, and preferably 3.8 cm;
- width b-c of the front arms E: between 1.0 and 3.0 cm and preferably 2.0 cm;
- length d-y of the front portion A: between 2.5 and 6.5 cm, and preferably 4.0 cm;
- total length d-z of the device: between 11 and 15 cm, and preferably 12 cm;
- distance y-x in the central hole U: between 0.6 and 1.6 cm, and preferably 1.1 cm;
- distance x-e in the central hole U, the same as or different from the distance y-x: between 0.6 and 1.6 cm, and preferably 1.1 cm;
- length e-f of the rear portion D: between 1.8 and 4.0 cm, and preferably 2.3 cm;
- width x-l: between 0.5 and 4.0, and preferably 2.5 cm;
- distance h-h between the rear arms F: between 1.5 and 7.0 cm; for devices to be implanted in patients of a small size it is typically between 1.5 and 5.5 cm and is preferably 3.5 cm, while for devices to be implanted in patients of a large size it is between 3.0 and 7.0 cm and is preferably 5.0 cm;
- distance g-g between the rear arms F: between 4.9 and 10 cm; for devices to be implanted in patients of a small size it is typically between 4.9 and 8.9 cm and is preferably 6.0 cm, while for devices to be implanted in patients of a large size it is between 6.0 and 10 cm and is preferably 7.6 cm;
- distance i-i between the rear arms F: between 4.5 and 10.5 cm; for devices to be implanted in patients of a small size it is typically between 4.5 and 8.5 cm and is preferably 6.5 cm, while for devices to be implanted in patients of a large size it is between 6.5 and 10.5 cm and is preferably 8.0 cm;
- length h-i of the rear arms F: between 2.5 and 6.5 cm, and preferably 4.5 cm.

The dimensions of the device according to the invention without a hole illustrated in FIG. 4, are the same as given above for the embodiments illustrated in FIGS. 1-3, except for the length h-i of the rear arms and therefore for the total length d-z of the device.

In facts, the device illustrated in FIG. 4, depending on whether it is to be implanted in patients with partial prolapse or in patients without uterus with prolapse of the vaginal vault, may have rear arms of different lengths.

A device suitable in the case of partial prolapse has for example the following dimensions:
- total length d-z of the device: between 4 and 8 cm, and preferably 5.1 cm;
- length h-i of the rear arms F: between 0.5 and 3 cm, and preferably 1.1 cm; while the device suitable in cases of prolapse of the vaginal vault has the following dimensions:
- total length d-z of the device: between 10 and 13 cm, and preferably 11 cm;
- length h-i of the rear arms F: between 2.5 and 6.5 cm, and preferably 4.5 cm.

The device according to the invention must be made of a material having a reticular or laminar structure, so as not to retain exudates and organic liquids which could build up on the central body of device, in particular in area A.

Any material having a reticular or laminar structure, whether it be of organic or synthetic origin, is suitable for the realisation of the present device as long as it maintains its structure more or less unchanged over time and remains fixed in the position in which it was inserted during surgery.

Numerous synthetic materials are currently on the market which could be used to make the present device, for example materials based on single-filament polypropylene for use in surgical implants, in particular the reticular materials composed of mixtures of polypropylene and polyglactin.

Materials of organic origin that could be used according to the invention are for example membrane of bovine pericardium, human fascia lata, acellular matrix of pig collagen, and submucosa of pig small intestine, suitably treated so as to be sterile and unable to transmit animal pathologies, and to remain more or less unaltered over time.

Examples of commercial product of organic origin that could be used according to the invention are for example membrane of bovine pericardium treated with glutaraldehyde and heparin, produced by Shelhigh and marketed under the name Dome Pericardial Patch No-React® Treated, pig intestine submucosa produced by DePuy OrthoTech and known by the trade name SIS (small intestine submucosa), or reticular porcine collagen marketed by Bard under the name Pelvicol®.

The materials of organic origin are preferably used in the realization of the present device as they are generally well tolerated by the organism, they do not give foreign body reactions, they are soft and impalpable and there is minimum risk of erosion of the tissues with which they come in contact, these materials thus being biocompatible.

The dimensions of the holes in the materials that may be used according to the invention have a diameter preferably comprised between 0.01 cm and 0.05 cm and more preferably 0.03 cm, at a distance from each other preferably of between 0.06 and 0.1 cm, and more preferably 0.08 cm.

The present device is applied by surgery; during surgery, the habitual means of access is the vagina, with an incision extending from the front vaginal wall to the rear wall, excluding the neck of the uterus.

Through the front vaginal wall the tendinous arch of the levator ani is penetrated, which is opened bilaterally for about 2 cm, and on which the two arms E are fixed respectively on the right and on the left.

The two rear arms F are then passed by the sides of the neck of the uterus, one on the right and one on the left, and are laid until the central part B surrounds the neck of the uterus. The right and the left half of the rear portion of the device are rejoined in the centre with two stitches and the rear arms are fixed bilaterally to the sacrospinous ligament or to the iliococcygeal muscle. At the end of the operation the device, anchored by means of the four arms to the tendinous arch of the levator ani and to the sacrospinous ligament (or to the iliococcygeal muscle), is at the normal anatomical level of the levator ani muscle. Consequently, also the organs resting on it, the bladder at the front (cystocele), the neck of the uterus in the centre (hysterocele, the rectum at the rear (enterocele), are returned to their correct anatomical plane above said muscle.

The operation can also be carried out by fixing first the two rear arms, using the device in which the cleft extends longitudinally from the central hole, cutting the front portion A.

Alternatively, the device according to the invention may be used which has the cleft H both in the front part and in the rear, and is therefore composed of two specular halves; in this case the operation is carried out by fixing first one half through the two front and rear arms and then the other half; the two halves already fixed both at the front and at the rear are then rejoined on the front portion A and on the rear portion D, taking care to position the neck of the uterus in the central hole U.

In the case of the device with a horizontal cleft, the procedures for passing around the neck of the uterus are the same as described above for the devices with a longitudinal cleft, and the suture of the cut of the device will be in a lateral position.

In patients without uterus, the operation may be carried out using the device represented in FIG. 3, fixing first the front arms and then the rear arms, or vice versa.

Moreover, in patients suffering of a partial prolapse of pelvic organs, the operation may be carried out by using the device illustrated in FIG. 4; in this case the vaginal surgery procedure comprises making an incision extending from the front vaginal wall to the cervix; penetrating the tendinous arch of the levator ani through the front vaginal wall; bilaterally opening said tendineous arch for about 2 cm; fixing the two front arms of the said device respectively on the right and on the left on the said opened tendineous arch; and bilaterally fixing the rear short arms to the neck of the uterus.

All the cases described above may also be realised by means of "tension free" operations, in which the present device is positioned inside the vaginal cavity without fixing it with stitches, but only making dissections in the tendinous arch of the levator ani which guarantee the positioning of the front arms E. In this type of "tension free" operation the device according to the invention must have the opening of the front arms, represented in the figures by the length a-a, between 11 and 15 cm; moreover, it is preferable to use devices made of polypropylene and similar.

Moreover, as well as by the only vaginal approach, the operation may be carried out with a mixed vaginal/abdominal or vaginal/laparoscopical approach, or by means of mini-invasive surgery.

The invention being as described, it is clear that this device may be modified in various ways; these modifications are not to be considered as divergences from the spirit and from the prospects of the invention and all those modifications which would appear evident to an expert in the field are included within the scope of the following claims.

I claim:

1. A method for surgically implanting a flat implantable device made of material with a reticular structure for supporting the female pelvic organs, having a central body with a trapezoid shape with small and large bases and four arms, comprising:
   an anterior portion corresponding to the smaller base of the trapezium, from the ends of which branch off two anterior arms;
   a central portion corresponding to the central part of the trapezium;
   a posterior portion corresponding to the larger base of the trapezium, from the ends of which branch off two posterior arms diverging from each other and parallel to the sides of the trapezium;
   characterized in that the said two anterior arms branch off from the anterior portion in opposite directions and are generally coaxial with each other and generally parallel to said smaller base; and the said central portion has a central hole from which starts a cleft,
   wherein, when the said device is inserted into the vaginal cavity of the patient by means of vaginal surgery, said method comprises: making an incision extending from the anterior vaginal wall to the posterior vaginal wall; penetrating the tendinous arch of the levator ani through the anterior vaginal wall; bilaterally opening said tendineous arch for about 2 cm; fixing the two anterior arms of the said device respectively on the right and on the left on the said opened tendineous arch; and bilaterally fixing the posterior arms to the sacrospinous ligament or to the iliococcygeal muscle.

2. An implantable device made of soft sheet material with a reticular structure insertable by vaginal surgery into a female pelvis for supporting female pelvic organs, comprising:
   (a) a central body having opposite anterior and posterior portions having anterior and posterior terminal edges respectively, and having opposite sides each with a terminal side edge, about a central longitudinal axis, said sides defining between them a width the maximum dimension of which is designated w,
   (b) a pair of anterior arms extending symmetrically outward from said anterior portion transversely of said central longitudinal axis, said anterior arms having terminal ends spaced apart from each other a distance greater than W, (c) a pair of posterior arms extending symmetrically downward from said central body and diverging from each other and having terminal ends spaced apart from each other a distance greater than W, (d) said central body having a hole extending through said sheet material, said hole located between said anterior and posterior portions and generally centrally between said sides, said central body including a cleft extending from said hole rearward to said terminal posterior edge.

3. A device according to claim 2 wherein said anterior arms extend generally coaxially.

4. A device according to claim 2 wherein said anterior arms extend generally perpendicularly to said central longitudinal axis.

5. A device according to claim 2 wherein each of said arms is elongated about an arm central axis, and each of said arms has a proximal portion adjacent said central body and a distal portion, and for each of said arms its proximal portion has breadth greater than the breadth of its distal portion.

6. A device according to claim 5 wherein each of said anterior and posterior arms is tapered along its length to have a smaller distal portion than its proximal portion.

7. A device according to claim 2 wherein said sheet material with a reticular structure has extending transversely through it holes having diameter in the range of 1 to 7 mm and spaced apart from each other a distance in the range of 0.05 to 0.10 cm.

8. An implantable device made of soft sheet material with a reticular structure for supporting female pelvic organs when inserted by vaginal surgery, comprising:

a central body having opposite anterior and posterior portions having anterior and posterior terminal edges respectively, and having opposite sides each with a terminal side edge, about a central longitudinal axis, said sides defining between them a width the maximum dimension of which being designated W, a pair of anterior arms extending symmetrically outward from said anterior portion transversely of said central longitudinal axis, said anterior arms having terminal ends spaced apart from each other a distance greater than W, a pair of posterior arms extending symmetrically downward from said central body and diverging from each other and having terminal ends spaced apart from each other a distance greater than W, said central body having a hole extending through said sheet material, said hole located coaxially with said central longitudinal axis and between said anterior and posterior portions and generally centrally between said terminal side edges, said central body including a cleft extending from said hole to one of said anterior and posterior terminal edges or to one of said opposite terminal side edges.

9. The device according to claim 8, wherein said material with a reticular structure is selected from the group consisting of materials of organic origin and materials of a synthetic nature.

10. An implantable device made of soft sheet material with a reticular structure insertable by vaginal surgery into a female pelvis for supporting female pelvic organs, comprising:

a central body having a generally trapezoidal shape with small and large bases generally parallel to each other, two opposite side edges, said central body comprising an anterior portion with an anterior edge that is said small base and a posterior portion with a posterior edge that is said large base, a pair of anterior arms extending symmetrically and generally coaxially outward from said anterior portion, a pair of posterior arms extending symmetrically and downward from said central body's posterior portion and diverging from each other, said central body having a hole extending through said sheet material, said hole located generally centrally between and inwardly of said sides and between said anterior and posterior edges, said central body including a cleft extending from said hole to one of said anterior and posterior edges or to one of said opposite side edges.

11. A device according to claim 10 wherein, (a) said anterior arms have opposite ends that are spaced apart from each other a distance designated a-a between 8 and 15 cm., (b) said smaller base has length designated b-b between 3 and 6 cm., (c) said device has total length designated d-z between 11 and 15 cm., (d) said larger base has length designated h-h between 5 and 10 cm., (e) said posterior arms have opposite ends spaced apart from each a distance designated i-i, between 6 and 12 cm., and (f) said central hole designated U has diameter designated y-e between 1.2 and 3.2 cm.

12. An implantable device made of soft sheet material with a reticular structure insertable by vaginal surgery into a female pelvis for supporting female pelvic organs, comprising:

a central body having an anterior portion with an anterior edge and a posterior portion with a posterior edge, and two opposite side edges, a pair of anterior arms extending symmetrically and generally coaxially outward from said anterior portion, a pair of posterior arms extending symmetrically and downward from said posterior portion and diverging from each other, said central body having a hole extending through said sheet material, said hole located generally centrally between and inwardly of said side edges and between said anterior and posterior edges, said central body including a cleft extending from said hole to one of said anterior and posterior edges or to one of said opposite side edges.

13. A method for surgically implanting a device in a female patient suffering a partial or total prolapse of pelvic organs into the vagina, where said device made of soft sheet material with a reticular structure for supporting female pelvic organs when inserted by vaginal surgery, includes:

a central body having opposite anterior and posterior portions having anterior and posterior terminal edges respectively, and having opposite sides each with a terminal side edge, about a central longitudinal axis, said sides defining between them a width the maximum dimension of which being designated W, a pair of anterior arms extending symmetrically outward from said anterior portion transversely of said central longitudinal axis, said anterior arms having terminal ends spaced apart from each other a distance greater than W, a pair of posterior arms extending symmetrically downward from said central body and diverging from each other and having terminal ends spaced apart from each other a distance greater than W, said central body having a hole extending through said sheet material, said hole located coaxially with said central longitudinal axis and between said anterior and posterior portions and generally centrally between said terminal side edges, said central body including a cleft extending from said hole to one of said anterior and posterior terminal edges or to one of said opposite terminal side edges, said method comprising:

(a) making an incision oriented generally axially of the vaginal cavity in the anterior vaginal wall while excluding the neck of the uterus, and electing to make a separate similar incision in the posterior vaginal wall excluding the neck of the uterus, either before making said anterior wall incision or later in the operation, (b) reaching through said anterior wall incision and bilaterally opening the pubo-cervical fascia, (c) through said opening of the pubo-cervical fascia reaching the tendinous arch of the levator ani, (d) inserting the anterior arms and the anterior portion of said device through the vaginal cavity, through said opening of the pubo-cervical fascia and positioning said anterior portion of said device under the patient's bladder, (e) fixing by stitches or staples the two anterior arms of said anterior portion of the device to the right and left tendineous arches, (f) making an axially oriented incision in the posterior vaginal wall excluding the neck of the uterus, if such incision has not already been made, (g) passing respectively said two posterior arms by the sides of the neck of the uterus, one on the right and one on the left until the central part of said device surrounds the neck of the uterus, (h) joining by stitches or staples the adjacent edges of the cleft of the device, and (i) bilaterally fixing by stitches or staples the posterior arms of said device to the right and left sacrospinous ligaments respectively.

14. A method for surgically implanting a device in a female patient suffering a partial or total prolapse of pelvic organs into the vagina, a device made of soft sheet material with a reticular structure formed as a central body having opposite anterior and posterior portions and opposite sides, a pair of anterior arms extending symmetrically outward from said anterior portion, a pair of posterior arms extending symmetrically downward from said posterior portion, with a hole located inwardly from said anterior, posterior and side edges, and a cleft defined by adjacent edges extending from said hole to one of said anterior, posterior and side edges, comprising:

(a) making an incision oriented generally axially of the vaginal cavity in the posterior vaginal wall while excluding the neck of the uterus, and electing to make a separate similar incision in the anterior vaginal wall, excluding the neck of the uterus, either before making said posterior wall incision or later in the operation, (b) inserting the posterior arms and the posterior portion of said device through the vaginal cavity and bilaterally fixing by stitches or staples the posterior arms of the device to the sacrospinous ligaments respectively, (c) positioning the posterior portion of the device under the intestine and behind the cervix, (d) passing respectively said two anterior arms of the device by the sides of the neck of the uterus, one on the right and one on the left until the central body of the said device surrounds the neck of the uterus, (e) joining by stitches or staples said adjacent edges of the cleft, (f) bilaterally opening the pubo-cervical fascia, (g) through the anterior opening reaching the tendinous arch of the levator ani, (h) projecting the anterior portion of said device through the vaginal cavity and positioning it under the bladder, and (i) fixing by stitches or staples the two anterior arms of the said device respectively to the right and left tendineous arches.

15. A method for surgically implanting the device in a female patient suffering a partial or total prolapse of pelvic organs into the vagina, where said device made of soft sheet material with a reticular structure for supporting female pelvic organs when inserted by vaginal surgery, includes:

a central body having opposite anterior and posterior portions having anterior and posterior terminal edges respectively, and having opposite sides each with a terminal side edge, about a central longitudinal axis, said sides defining between them a width the maximum dimension of which being designated W, a pair of anterior arms extending symmetrically outward from said anterior portion transversely of said central longitudinal axis, said anterior arms having terminal ends spaced apart from each other a distance greater than W, a pair of posterior arms extending symmetrically downward from said central body and diverging from each other and having terminal ends spaced apart from each other a distance greater than W, said central body having a hole extending through said sheet material, said hole located coaxially with said central longitudinal axis and between said anterior and posterior portions and generally centrally between said terminal side edges, said central body including a cleft extending from said hole to one of said anterior and posterior terminal edges or to one of said opposite terminal side edges, said method comprising the steps:

(a) making an incision oriented generally axially of the vaginal cavity in the anterior vaginal wall while excluding the neck of the uterus, and electing to make a separate similar incision in the posterior vaginal wall excluding the neck of the uterus, either before making said anterior wall incision or later in the operation, (b) electing one of the following two steps to be done first, (i) fixing by stitches or staples the two anterior arms of said anterior portion of said device to the right and left tendineous arches, and (ii) bilaterally fixing by stitches or staples the posterior arms of said device to the right and left sacrospinous ligaments respectively, (c) passing respectively said two anterior or posterior arms corresponding to step (b)(i) or (b)(ii) above, by the sides of the neck of the uterus, one on the right and one on the left until the central body of said device surrounds the neck of the uterus, (d) joining by stitches or staples the adjacent edges of the cleft of the device, and (e) conducting the other of said two steps in paragraph (b).

16. A method for surgically implanting the device in a female patient suffering a partial or total prolapse of pelvic organs into the vagina, where said device made of soft sheet material with a reticular structure for supporting female pelvic organs when inserted by vaginal surgery, includes:

a central body having opposite anterior and posterior portions having anterior and posterior terminal edges respectively, and having opposite sides each with a terminal side edge, about a central longitudinal axis, said sides defining between them a width the maximum dimension of which being designated W, a pair of anterior arms extending symmetrically outward from said anterior portion transversely of said central longitudinal axis, said anterior arms having terminal ends spaced apart from each other a distance greater than W, a pair of posterior arms extending symmetrically downward from said central body and diverging from each other and having terminal ends spaced apart from each other a distance greater than W, said central body having a hole extending through said sheet material, said hole located coaxially with said central longitudinal axis and between said anterior and posterior portions and generally centrally between said terminal side edges, said central body including a cleft extending from said hole to one of said anterior and posterior terminal edges or to one of said opposite terminal side edges, said method comprising:

making an axially oriented incision in the anterior vaginal wall while excluding the neck of the uterus, and electing to make a separate longitudinal incision in the posterior vaginal wall excluding the neck of the uterus, either before making said anterior wall incision or later in the operation, electing the sequence I or sequence II steps, where sequence I comprises:

(a) inserting said device into the vaginal cavity and inserting the anterior arms through said anterior vaginal wall incision and positioning a portion of said device under the patient's bladder, (b) fixing by stitches or staples the two anterior arms of said anterior portion of said device to the right and left tendineous arches, (c) passing respectively said two posterior arms by the sides of the neck of the uterus, one on the right and one on the left until the central part of said device surrounds the neck of the uterus, (d) joining by stitches or staples the adjacent edges of the cleft of the device, and (e) bilaterally fixing by stitches or staples the posterior arms of said device to the right and left sacrospinous ligaments respectively, and sequence II comprises:

(f) inserting said device into the vaginal cavity and inserting the posterior arms through said posterior vaginal wall incision, (g) bilaterally fixing by stitches or staples the posterior arms of said device to the right and left sacrospinous ligaments respectively, (h) passing respectively said two anterior arms by the sides of the neck of the uterus, one on the right and one on the left until the central body of said device surrounds the neck of the uterus (i) joining by stitches or staples the adjacent edges of the cleft of the device, and (j) fixing by stitches or staples the two anterior arms of said anterior portion of said device to the right and left tendineous arches.

* * * * *